United States Patent [19]

Zaugg et al.

[11] 4,083,868
[45] Apr. 11, 1978

[54] 2-(α-AMIDOBENZYL)-5-ALKYLRESORCINOLS

[75] Inventors: Harold Elmer Zaugg, Lake Forest; Cheuk Man Lee, Libertyville, both of Ill.

[73] Assignee: Abbott Laboratories, North Chicago, Ill.

[21] Appl. No.: 714,865

[22] Filed: Aug. 16, 1976

[51] Int. Cl.² .................................... C07C 103/38
[52] U.S. Cl. .................. 260/562 N; 260/562 B; 260/562 P; 260/562 A; 260/293.76; 424/324; 424/246; 424/248.54; 424/267
[58] Field of Search .......... 260/562 N, 562 B, 562 P, 260/562 A

[56] References Cited
PUBLICATIONS

Okada et al., Tetrahedron 26 (1970), pp. 3661, 3662, 3664, 3665.

Primary Examiner—Arthur P. Demers
Attorney, Agent, or Firm—Paul D. Burgauer; Robert L. Niblack

[57] ABSTRACT

A compound of the formula

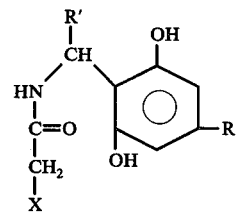

wherein R is a $C_6$–$C_{20}$ alkyl, arylalkyl or cycloalkyl alkyl; R' is phenyl or substituted phenyl; and X is H, halogen, $N(R'')_2$ where R'' is H or $C_1$–$C_7$ alkyl, or a group represented by the formula

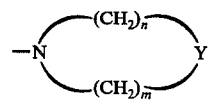

where $n$ is an integer from 1 to 4; $m$ is an integer from 1 to 4; and Y is $CH_2$, O, S or NR''' where R''' is H or $C_1$–$C_7$ alkyl.

The compounds of this invention are useful as intraocular pressure lowering agents, i.e., anti-glaucoma agents.

4 Claims, No Drawings

2-(α-AMIDOBENZYL)-5-ALKYLRESORCINOLS

SUMMARY OF THE INVENTION

The present invention is related to 5-alkylresorcinols and more particularly to 2-(α-amidobenzyl)-5-alkylresorcinols which are useful as intra-ocular pressure lowering agents.

By using the α-amidoalkylation reaction of a benzylidenebisamide with a 5-alkylresorcinol, a 2-(α-amidobenzyl)-5-alkylresorcinol is provided according to the present invention.

DETAILED DESCRIPTION OF THE INVENTION

This invention relates to 2(α-amidobenzyl)-5-alkylresorcinola which are useful as intra-ocular pressure lowering agents. The 5-alkylresorcinols are compounds represented by the structural formula:

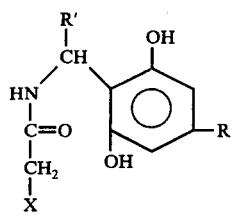

wherein R is a $C_6$–$C_{20}$ alkyl, arylalkyl or cycloalkyl alkyl; R' is phenyl or substituted phenyl; and X is H, halogen,

where R'' is H or $C_1$–$C_7$ alkyl, or a group represented by the formula

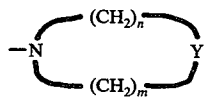

where n is an integer from 1 to 4; m is an integer from 1 to 4; and Y is $CH_2$, O, S or NR''' where R''' is H or $C_1$–$C_7$ alkyl.

The term "$C_6$–$C_{20}$ alkyl" as used herein refers to both straight and branched chain alkyl radicals, including n-hexyl, n-heptyl, 3-methyl-2-octyl, n-octyl, n-nonyl, 2-tetradecyl, 2-eicosanyl, and the like.

The term "arylalkyl" refers to the alkyl group of 1 to 10 carbon atoms where one of the hydrogen atoms of the alkyl group is substitited by phenyl or a substitited phenyl.

Cycloalkyl, as used herein, refers to cyclic, saturated aliphatic radicals having 3 to 8 carbon atoms in a ring, such as cyclopropyl, cyclobutyl, cyclopentyl, cyclohexyl, cycloheptyl and cyclooctyl.

"Cycloalkyl alkyl" refers to groups such as cyclopropyl-methyl 2-methylcyclobutyl and the like.

The compounds of this invention exhibit activity as intra-ocular pressure lowering agents. The activity of lowering the intra-ocular pressure is obtained in dosages from 0.5 to 2.5 mg/kg of body-weight orally and from 0.1 to 1.0 mg/kg body-weight interperitoneally (i.p.).

The compounds of the present invention may be prepared by means of a variety of techniques. For example, the 5-alkylresorcinola or homologues thereof can generally be prepared by the α-amido-alkylation of a 5-alkylresorcinol (4) with a benzylidenebisamide (1), to provide the respective 2-(α-amidobenzyl)-5-alkylresorcinol (5). The procedure with the initial preparation of the present compounds is illustrated in the flow diagram below (Scheme I):

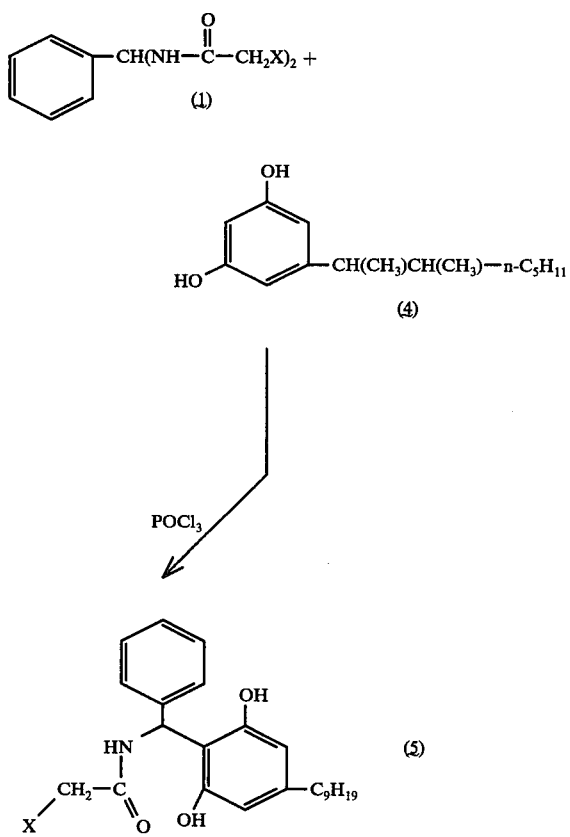

where X is as defined above.

Other derivatives and homologues of the present invention may be prepared by treatment of 2-(α-chloroacetyl-aminobenzyl)-5-(3-methyl-2-octyl)-resorcinol (7) with dimethylamine and piperidine to provide the desired resorcinol (8). The treatment of the resorcinol (7) with dimethylamine and piperidine, which provides the desired resorcinol (8), is shown in the flow diagram below (Scheme II):

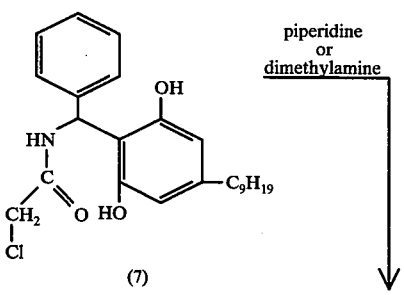

-continued

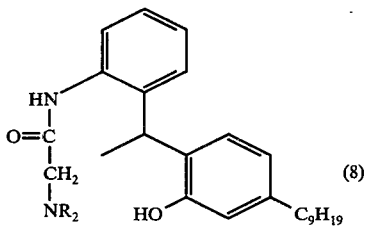

where NR₂ is as defined above.

In Scheme (I), illustrated above, the benzylidenebisamides
(1) that may be used include:
(2) N,N'-benzylidenebisacetamide and
(3) N,N'-benzylidenebischloroacetamide;
and the 2-α-amidobenzyl)-5-alkylresorcinols (5) produced include:
(6) 2-(α-acetylaminobenzyl)-5-(3-methyl-2-octyl)-resorcinol; and
(7) 2-(α-chloroacetylaminobenzyl)-5-(3-methyl-2-octyl) -resorcinol.

And, in Scheme (II), the resulting resorcinols (8) include:
(9) 2-(α-dimethylaminoacetylaminobenzyl)-5-(3-methyl-2-octyl)-resorcinol hydrochloride; and
(10) 2-(α-piperidinoacetylaminobenzyl)-5-(3-methyl-2-octyl)-resorcinol hydrochloride.

The following examples further illustrate the present invention:

EXAMPLE 1

2-(α-Acetylaminobenzyl-5-(3-methyl-2-octyl)-resorcinol (6)

A stirred solution-suspension of 11.8 g (0.05 mol) of 5-(3-methyl-2-octyl)-resorcinol (4) (65% dl-erythro and 35% dl-threo) and 10.7 g (0.052 mol) of N,N'-benzylidenebisacetamide (2) in 60 ml of methylene chloride cooled to 2° in an ice bath was treated dropwise with 4.9 ml (0.05 mol) of phosphorus oxychloride over a period of 5 to 10 minutes. The stirring was continued in the melting ice bath. A clear solution formed after 2 to 2.5 hours and precipitation of produce occurred after 3 to 3.5 hours. After being stirred at room temperature overnight, the reaction mixture was treated with water (40 ml) and more methylene chloride (70 ml). After the slight exothermic reaction was complete, the organic layer containing suspended product was separated and washed successively with water (2 × 100 ml), 5% sodium bicarbonate (100 ml), and water (100 ml). Filtration of the organic layer gave 5.00 g of colorless crystalline powder, mp 204–208°. Concentration of the filtrate and cooling gave 2.58 g, mp 196–199°, as a second crop (7.58 g = 40% yield). Concentration to dryness left 10.8 g of an amorphous glassy solid which could not be crystallized. Its pmr spectrum was similar to that of the crystalline fraction, suggesting it consisted of a mixture of stereoisomers. Recrystallization from acetonitrile of a sample of the 7.58 g to constant mp gave pure 2-(α-acetylaminobenzyl)-5-(3-methyl-2-octyl)-resorcinol (6) mp 209°–210° (probably a single stereo-isomer); ir (Nujol) 3400 (νNH or OH), 3200 (broad, ν bonded OH), and 1610 cm⁻¹(νC=O); pmr (DMSO-d₆) δ 9.0 –9.8 (m, 2H, OH), 7.98 (d, 1H, J = 9 Hz, NH), 7.0 – 7.5 (m, 5H, C₆H₅), 6.64 (d, 1H, J = 9 Hz, Ar₂CHNH), 6.18 (s, 2H, C₆H₂) and 1.92 ppm (s, 3H, CH₃CO); m/e (M⁺) 383.

Anal. (C₂₄H₃₃NO₃) C, 75.16; H, 8.67; N, 3.65. Found: C, 74.85; H, 8.98; N, 3.59.

EXAMPLE 2

2(α-Dimethylaminoacetylaminobenzyl)-5-(3-methyl-2-octyl)-resorcinol hydrochloride (9)

Phosphorous oxychloride (4.0 ml, 0.042 mol) was added dropwise to a stirred solution of 14.3 g (0.052 mol) of N,N'-benzylidenebischloroacetamide (3) and 11.8 g (0.05 mol) of (4) in 400 ml of dry methylene chloride cooled in an ice bath. After stirring at room temperature for 65 hrs, the reaction mixture was worked up as described for the preparation of (6). There was obtained 19.5 g of amorphous glassy product which could not be crystallized, but whose spectral properties (ir and pmr) corresponded to the structure of 2-(α-chloroacetylaminobenzyl)-5-(3-methyl-2-octyl)-resorcinol (7).

A solution of 3.65 g of this crude product in 40 ml of dioxane was added dropwise to a stirred solution of 12 g of dimethylamine in 50 ml of dioxane cooled in an ice bath. After stirring for 72 hrs at room temperature, the reaction mixture was filtered and the filtrate was concentrated in vacuo in a rotary evaporator. The residue was taken up in chloroform, washed with water, and dried over anhydrous sodium sulfate. Filtration and removal of the solvent by distillation gave an oil (4.4 g) which was chromatographed on a Florisil column (150 g, 60–100 mesh) using graded methanol-chloroform mixtures for elution. The resulting main fraction (1.76 g) was still an oil which was taken up in dry ether, treated with dry hydrogen chloride and collected at the filter. Recrystallization from ethanol-ether gave 1.0 g of 2-(α-dimethylaminoacetylaminobenzyl)-5-(3-methyl-2-octyl)-resorcinol hydrochloride(9), mp 199°–201°.

Anal. (C₂₆H₃₉ClN₂O₃) C, 67.44; H, 8.49; N,6.05. Found: C, 67.12; H, 8.63; N, 6.06.

EXAMPLE 3

2-(α-Piperidinoacetylaminobenzyl)-5-(3-methyl-2-octyl)-resorcinol hydrochloride (10)

A solution of 4.18 g (0.01 mol) of crude 2-(α-chloroacetylaminobenzyl)-5-(3-methyl-2-octyl)-resorcinol (7) and 4.25 g (0.05 mol) of piperidine in 30 ml of methanol was heated under reflux for 3 hrs and worked up as described above for the preparation of 2-(α-dimethylaminoacetylaminobenzyl)-5-(3-methyl-2-octyl)-resorcinol hydrochloride (9). There was obtained 1.9 g of (10), mp 195°–198° (from ethanol-ether).

Anal. (C₂₉H₄₃ClN₂O₃) C, 69.22; H, 8.61; N, 5.56. Found C, 69.53; H, 8.72; N, 5.62.

EXAMPLE 4

Effectiveness in Reducing Intra-Ocular Pressure

In determining the efficacy of the present compounds in reducing intra-ocular pressure, unanesthetized male albino rabbits were used. The rabbits weighed between 2.0 and 4.0 kg. and were restrained in plastic devices. A Bausch and Lomb Applamatic Tomometer was used to measure intra-ocular pressure. Three control pressure measurements, consisting of three aprproximately equal readings for each eye, were made at 30 minute intervals, The compounds used in this test were epinephrine, 2-(α-acetylaminobenzyl-5-(3-methyl-2-octyl)-resorcinol (6), 2-(α-dimethylaminoacetylaminobenzyl)-5-(3-methyl-2-octyl)-resorcinol hydrochloride (9) and 2-(α- piperidinoacetylaminobenzyl)-5-(3-methyl-2-octyl)-resorcinol hydrochloride (10). The test compounds were prepared in propylene glycol and applied topically to the eyes of the rabbits. The compounds were applied in 0.1% solutions and the volume instilled into the conjunctival sac was constant at 0.1 ml. Pressure readings were made at 30, 60, 90, 120 and 180 min after drug application. The average reductions of the intra-ocular pressure in the rabbits as effected by the respective compounds are provided below in Table I.

TABLE I

| Effect of Compounds in Reducing Intra-Ocular Pressure in Rabbits | |
|---|---|
| Compound (0.1% Solution) | Average Reduction (%) |
| Epinephrine | 24 |
| (6) | 23 |
| (9) | 30 |
| (10) | 18 |

We claim:
1. A compound of the formula

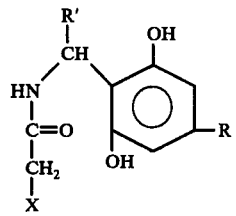

wherein
R is a $C_6$–$C_{20}$ alkyl, arylalkyl or cycloalkyl alkyl;
R' is phenyl ; and X is H, halogen, or N $(R'')_2$ where R'' is H or $C_1$–$C_7$ alkyl.

2. A compound according to claim 1, wherein R is an alkyl of 9 carbon atoms, R' is phenyl and X is H.

3. A compound according to claim 1, wherein R is an alkyl of 9 carbon atoms, R' is phenyl and X is Cl.

4. A compound according to claim 1, wherein R is an alkly of 9 carbon atoms, R' is phenyl and X is N(R'') where R'' is $CH_3$.

* * * * *